United States Patent [19]

Bonaldi et al.

[11] 4,331,607

[45] May 25, 1982

[54] PROCESS FOR THE PURIFICATION OF CHENODEOXYCHOLIC ACID

[75] Inventors: Antonio Bonaldi, Schilpario; Egidio Molinari, Erba, both of Italy

[73] Assignee: Blasinachim S.p.A., Milan, Italy

[21] Appl. No.: 167,470

[22] Filed: Jul. 11, 1980

[30] Foreign Application Priority Data

Jul. 12, 1979 [IT] Italy .............................. 24315 A/79

[51] Int. Cl.$^3$ .............................................. C07J 9/00
[52] U.S. Cl. ................................................. 260/397.1
[58] Field of Search ..................................... 260/397.1

[56] References Cited

U.S. PATENT DOCUMENTS 3,931,256  1/1976  Saltzman ......................... 260/397.1
4,022,806  5/1977  Frost et al. ....................... 260/397.1

*Primary Examiner*—Ebert L. Roberts
*Attorney, Agent, or Firm*—Stevens, Davis, Miller & Mosher

[57] ABSTRACT

Process for preparing chenodeoxycholic substantially free from impurities and from solvents; crude chenodeoxycholic acid is subjected to crystallization from a solvent selected in the group consisting of mono- and polyhalogenated aliphatic hydrocarbons containing from 1 to 5 carbon atoms and that, if desired, the thus obtained product is dissolved in a water-miscible organic acid having low molecular weight and the thus obtained solution is poured into water, the precipitate is poured into water, the precipitate is collected by filtration, washed with water and dried.

5 Claims, No Drawings

PROCESS FOR THE PURIFICATION OF CHENODEOXYCHOLIC ACID

This invention relates to a process for the purification of crude chenodeoxycholic acid. Chenodeoxycholic acid is known since long time but only recently it has been used in human medicine owing to its gallstone dissolving activity. Chenodeoxycholic acid may be produced in a easy way by synthetic route but its purification is very difficult. In fact is contains, whichever is the synthetic route, a number of by-products which may be eliminated only with great difficulties.

A typical impurity is lithocholic acid whose structure is very close to the one of chenodeoxycholic acid, being only the 7-hydroxy group absent in lithocholic acid. On the other hand, the absence of lithocholic acid is a need because of its toxicity.

Some methods are known for the purification of chenodeoxycholic acid but none of them allows to reach satisfactory results.

According to the German unexamined and-open Application DOS No. 2,302,774 the purification is carried out by treating a methanolic solution of crude chenodeoxycholic acid with an inorganic salt of calcium or strontium and by separation of calcium or strontium salt of chenodeoxycholic acid. Chenodeoxycholic acid is then obtained by acidification, extraction with an organic solvent and removal of the organic solvent by distillation. This multi-steps method does not allow to obtain always the same results, even because some quantities of impurities remain incorporated in the salt which is precipitated and then they are not removed by the solvent.

A variation of the above mentioned method involves the formation of the sodium or potassium salt of chenodeoxycholic acid according to the U.S. Pat. No. 3,965,131. Since these salts are unsoluble in water, their aqueous solution is subjected to a continuous liquid-liquid extraction with a water immiscible organic solvent in order to remove the impurities contained in the crude chenodeoxycholic acid. Then the aqueous solution of the salt is processed in the usual way by acidification with an inorganic acid to form free chenodeoxycholic acid and by extracting the chenodeoxycholic acid with a water immiscible solvent, at last the solvent is removed by distillation.

This method, which is very difficult, allows to remove impurities of various kind but it is not suitable for removing lithocholic acid because lithocholic acid is easily salified to form alkaline salts which are soluble in water and their properties are substantially the same of chenodeoxycholic acid.

According to this invention crude chenodeoxycholic acid which contains also lithocholic acid as impurity is subjected to crystallization by using a solvent selected from the group consisting of mono- and polyhalogenated aliphatic hydrocarbons containing from 1 to 5 carbon atoms.

Suitable solvents according to this invention are chloroform, methylene chloride, dichloroethane, carbon tetrachloride, tetrachloroethane or mixtures thereof. A preferred embodiment is dichloroethane.

A method for the purification of chenodeoxycholic acid by crystallization, but not from halogenated solvents, is already known in the prior art. The French Open-Application No. 2.346.370 teaches how to purify chenodeoxycholic acid by crystallization from acetonitrile. However, this solvent does not remove lithocholic acid effectively; in addition it forms a solvate with the crystals of chenodeoxycholic acid and (it) can not be removed completely by evaporation. Furthermore, the use of acetonitrile allows to prepare only the crystalline form melting at 168°-170° C.

Pure chenodeoxycholic acid obtained according to this invention by crystallization from an halogenated aliphatic hydrocarbon has a solvent content lower than 0.3% and melts at 118°-120° C. If desired, the traces of solvents may be removed and the polymorphic form may be transformed into the one melting at 143°-145° C. by dissolving it in an organic acid having low molecular weight and water miscible like acetic and propionic acid. This solution is filtered, if necessary, and poured into a large quantity of deionized water maintained at room temperature and under continuous stirring. The precipitate is then collected by filtration, washed many times with water and dried in an oven under vacuum. The crystilline product thus obtained melts at 143°-145° C. and it is substantially free from impurities as well as from solvents.

The following examples are intended only to illustrate but not to limit this invention.

EXAMPLE 1

50 g of chenodeoxycholic acid containing 1% of lithocholic acid are dissolved in 500 ml of chloroform under heating. After filtration, the solution is cooled at 0° C. and kept under further stirring for two hours. The precipitate is collected by filtration, washed with cold chloroform and dried in an oven. Yield, 48 g of chenodeoxycholic acid melting at 118°-120° C. and containing less than 0.1% of lithocholic acid.

EXAMPLE 2

50 g of Chenodeoxycholic acid having a content of 0.1% of lithocholic acid are dissolved in 500 ml of dichloroethane by heating After filtration, the solution is cooled at 0° C. and kept under further stirring for two hours. The crystalline precipitate is collected by filtration, washed with cold dichloroethane and dried in an oven.

Yield, 45 g of chenodeoxycholic acid which is free from lithocholic acid when it is tested by T.L.C.

EXAMPLE 3

100 g of chenodeoxycholic acid of whichever polymorphic form are dissolved in 200 ml of acetic acid; the clear solution is poured in 2000 ml of deionized water under stirring. When the addition is complete the mixture is maintained under stirring for some hours till the mixture is as homogeneous as possible. The solid is collected by filtration and washed with 500 ml of water; after filtration the solid thus collected is washed with further 2000 ml of deionized water and dried in an oven at 80° C. under vacuum till its content of water is less than 0.5% when detected according to Karl Fischer's method.

Yield, 99.5 g of chenodeoxycholic acid melting at 143°-145° C. and substantially free from solvents when tested by gaschromatography.

What we claim is:

1. A process for preparing chenodeoxycholic acid substantially free from impurities and from solvents characterized in that crude chenodeoxycholic acid is subjected to crystallization from a solvent selected in the group consisting of mono- and poly-halogenated aliphatic hydrocarbons containing from 1 to 5 carbon atoms and that, if desired, the thus obtained product is dissolved in a water-miscible organic acid having low molecular weight and the thus obtained solution is poured into water, the precipitate is collected by filtration, washed with water and dried.

2. Process according to claim 1 characterized that the halogenated solvent is dichloroethane.

3. Process according to any of claims 1 and 2 characterized in that the water-miscible organic acid is acetic acid.

4. A process for preparing chenodeoxycholic acid substantially free from lithocholic acid which comprises crystallizing a crude chenodeoxycholic acid from a solvent selected from the group consisting of mono- and poly-halogenated hydrocarbons containing from 1 to 5 carbon atoms.

5. A process according to claim 4, in which the halogenated solvent is dichloroethane.

* * * * *